United States Patent [19]

Skarky

[11] 4,432,728
[45] Feb. 21, 1984

[54] DENTAL TRAY

[76] Inventor: Floyd E. Skarky, 2233 NW. 46th, Oklahoma City, Okla. 73112

[21] Appl. No.: 931,464

[22] Filed: Aug. 7, 1978

[51] Int. Cl.³ .............................................. A61C 9/00
[52] U.S. Cl. ...................................... 433/37; 433/44; 433/71
[58] Field of Search ................. 32/17, 18, 19; 433/37, 433/44, 71

[56] References Cited

U.S. PATENT DOCUMENTS

| | | | |
|---|---|---|---|
| 957,563 | 5/1910 | Kerr | 32/17 |
| 1,127,635 | 2/1915 | Kerr | 32/17 |
| 2,577,513 | 12/1951 | Cunningham | 32/17 |
| 3,247,844 | 4/1966 | Berghash | 32/17 |
| 3,537,179 | 11/1970 | Parker et al. | 32/17 |
| 3,574,259 | 4/1971 | Jones | 32/17 |
| 3,878,610 | 4/1975 | Coscina | 32/17 |
| 4,003,132 | 1/1977 | Beck | 32/17 |

FOREIGN PATENT DOCUMENTS 2754278 6/1978 Fed. Rep. of Germany .......... 32/17

*Primary Examiner*—John J. Wilson
*Attorney, Agent, or Firm*—Dunlap & Codding

[57] ABSTRACT

The present invention comprises a dental tray having a base extending in a dental arch an arcuate distance at least sufficient such that a portion of one surface of the base is disposable generally above some of the occlusal surfaces and such that a portion of the surface of the base is disposable generally above some of the incisal surfaces in one operating position of the dental tray. A lingual sidewall is connected to one side of the base and a buccal sidewall is connected to the opposite side of the base, each sidewall extending a surface molding distance generally perpendicularly from the base and the sidewalls cooperating with the base to form a space for accommodating molding and impression material.

2 Claims, 4 Drawing Figures

DENTAL TRAY

BACKGROUND OF THE INVENTION

1. Field of the Invention

The present invention relates to improvements in dental trays and, more particularly, but not by way of limitation, to an improved dental tray for use in such techniques as functionally generated path, soldering relation and porcelain occlusal matrix techniques, for example.

DESCRIPTION OF THE PREFERRED EMBODIMENT

Figure 1:
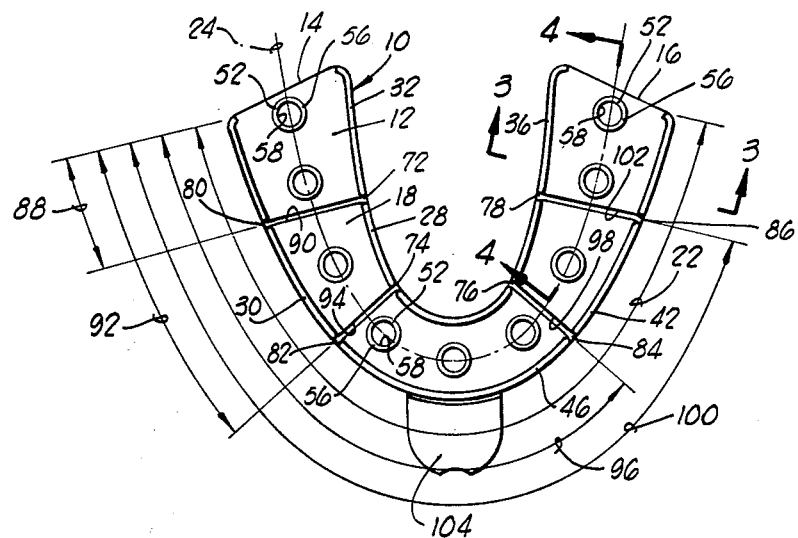
FIG. 1 is a top, plan view of the dental tray of the present invention.

Referring to the drawings in general and to FIGS. 1 through 4 in particular, shown therein and designated by the general reference numeral 10 is a dental tray constructed in accordance with the present invention.

The dental tray 10 includes a base 12 having opposite ends 14 and 16, a first surface 18, and a second surface 20. The base 12 extends in a dental arch an arcuate distance 22 generally between the opposite ends 14 and 16 of the base 12. The dental arch of the base 12 is diagrammatically represented in FIG. 1 via the centerline 24 and, as used herein, the term "dental arch" means the general arcuate shape formed in situ by an individual's upper or lower teeth (the dental arch includes either the upper dental arch, sometimes referred to in the art as the "maxillary arch", or the lower dental arch, sometimes referred to in the art as the "mandibular arch").

Figure 2:
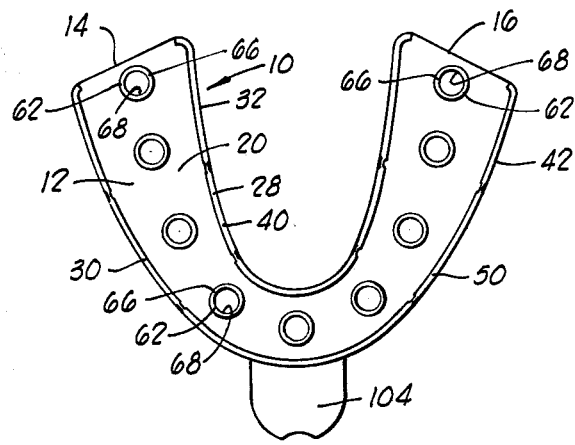
FIG. 2 is a bottom, plan view of the dental tray of FIG. 1.
Figures 3, 4:
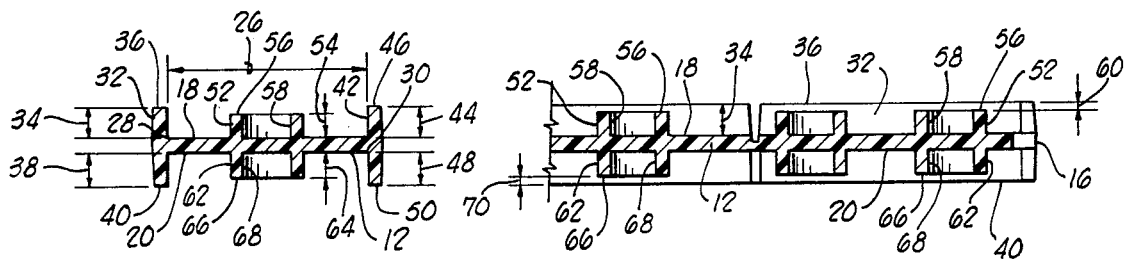
FIG. 3 is a cross sectional view of the dental tray of FIGS. 1 and 2, taken substantially along the lines 3—3 of FIG. 1.
FIG. 4 is a cross sectional view of the dental tray of FIGS. 1 and 2, taken substantially along the lines 4—4 of FIG. 1.

The base has a width 26 (shown in FIG. 3) extending generally between a lingual side 28 and a buccal side 30. As shown in FIGS. 1 and 2, the width 26 will vary slightly throughout the arcuate distance 22 generally between the opposite ends 14 and 16 of the base 12. However, the width 26 is greater than the width of either the occlusal surfaces or the incisal edges of an individual's teeth (in one form, the width 26 was about three-fourths of an inch near the ends 14 and 16 and the width 26 was about one-half inch at a position generally midway between the ends 14 and 16, for example). In this manner, when the dental tray 10 is disposed in an individual's mouth such that one surface 18 or 20 is disposed generally adjacent and above the bite surfaces of the individual's upper or lower teeth, the lingual side 28 of the base 12 extends a distance along the lingual side of the individual's teeth and the buccal side 30 of the base 12 extends a distance along the buccal side of an individual's teeth.

The term "lingual" as used herein to describe a portion of the dental tray 10 refers to a portion of the dental tray 10 disposed generally near an individual's tongue, as opposed to being near the individual's cheek or lips, when the dental tray 10 is placed in the individual's mouth in one operating position. On the other hand, the term "buccal" as used herein to describe a portion of the dental tray 10 refers to a portion of the dental tray 10 disposed near an individual's cheek or lips as opposed to being near the individual's tongue, when the dental tray 10 is placed in the individual's mouth in one operating position.

A lingual sidewall 32 is connected to the lingual side 28 of the base 12 and extends generally between the opposite ends 14 and 16 of the base 12. The lingual sidewall 32 extends a distance 34 generally perpendicularly from the first surface 18 terminating with an edge 36. In one preferred embodiment, the lingual sidewall 32 also extends a distance 38 generally perpendicularly from the second surface 20 of the base 12 terminating with an edge 40.

The dental tray 10 also includes a buccal sidewall 42 connected to the buccal side 30 of the base 12 and extending generally between the opposite ends 14 and 16 of the base 12. The buccal sidewall 42 extends a distance 44 generally perpendicularly from the first surface 18 terminating with an edge 46. In one preferred embodiment, the buccal sidewall 42 also extends a distance 48 from the second surface 20 of the base 12 terminating with an edge 50.

The edge 46 of the buccal sidewall 42 is generally coplanar with the edge 36 of the lingual sidewall 32 and the edge 50 of the buccal sidewall 42 is generally coplanar with the edge 40 of the lingual sidewall 32 in an assembled position of the dental tray 10. Thus, the distance 44 is substantially the same as the distance 34 and the distance 48 is substantially the same as the distance 38, the distances 34, 38, 44 and 48 all being substantially the same.

The distances 34, 38, 44 and 48 are important with respect to distinguishing the present invention from other prior art dental trays. The distances 34 and 44 are sized such that the portions of the sidewalls 32 and 42 extending the distances 34 and 44, respectively, from the first surface 18 cooperate with the first surface 18 of the base 12 to form a space for accommodating molding material. The dental tray 10 of the present invention is particularly constructed to assist in making molded models of the bite surfaces (occlusal surfaces and incisal edges) of an individual's teeth or models of certain information related to the bite surfaces (occlusal surfaces and incisal edges) of an individual's teeth. In applications of this type, it is important that the molding material not be pressed into the spaces between adjacent teeth particularly near an individual's gum since it would be extremely difficult to remove the dental tray 10 with the molding material from the individual's teeth without destroying the resulting model if the molding material were allowed to set or harden in the spaces between adjacent teeth. Thus, the distances 34 and 44 extend a minimum distance from the first surface 18 to accommodate a sufficient amount of molding material, but the distances 34 and 44 must be sufficiently small so the edges 36 and 46 are spaced a distance from the individual's gum when the dental tray 10 is in an operating position in the individual's mouth with the first surface 18 disposed generally near and spaced a distance from the bite surfaces (occlusal surfaces and incisal edges) or, in other words, so the sidewalls 32 and 42 extend a minimum distance along the lingual and buccal edges of an individual's teeth while still functioning to cooperate with the first surface 18 to accommodate a sufficient amount of molding material. In one embodiment, it has been found that the distances 36 and 46 are each about one-eighth of an inch. The distances 36 and 46 sized in the manner just described are each sometimes referred to herein as the "surface molding distance" for clarity.

The portions of the sidewalls 32 and 42 extending the distances 38 and 48, respectively, from the second surface 20 cooperate with the second surface 20 of the base 12 to form a space for accommodating molding material. The distances 38 and 48 are sized in a manner exactly like that just described with respect to the distances 34 and 44, and thus the distances 38 and 48 are each sometimes referred to herein as the "surface molding distance".

The term "bite surface" as used herein means the surfaces of a human's teeth which generally abut when the upper and the lower teeth are brought into a bite position. These surfaces are generally referred to in the art as the "occlusal surfaces" with respect to the upper and lower molars, bicuspids and canines, and the "incisal edges" with respect to the upper and lower incisors. Thus, the term "bite surface" as used herein includes the occlusal surfaces and the incisal edges.

One end of each of a plurality of cylindrically shaped first projections 42 is secured to the surface 18 of the base 12, each of the first projectons 52 extending a distance 54 (shown in FIG. 3) generally perpendicularly from the base 12 and terminating with an upper edge 56 (only some of the first projections 52 being designated via a reference numeral in the drawings). Each of the first projections 52 includes an opening 58, each of the openings 58 extending through one of the first projections 52 and intersecting the edge 56 thereof. The distance 54 is less than the distances 34 or 44 and, thus, the edges 56 are disposed in a plane spaced a distance 60 (shown in FIG. 4) generally below the planar disposition of the edges 36 and 46 of the lingual sidewall 32 and the buccal sidewall 42, respectively. The first projections 52 are spaced about the surface 18 generally between the opposite ends 14 and 16 of the base 12 and the first projections 52 cooperate to provide additional surface area for the molding material to enhance the adherence of the molding material to the dental tray 10 during the operation.

One end of each of a plurality of cylindrically shaped second projections 62 is secured to the surface 20 of the base 12 and each of the second projections 62 extends a distance 64 (shown in FIG. 3) generally perpendicularly from the surface 20 terminating with an edge 66 (only some of the second projections 62 being designated via a reference numeral in the drawings). An opening 68 is formed through each of the second projections 62, each opening 68 intersecting the edge 66 of one of the second projections 62. The distance 64 is less than either of the distances 38 or 48 and, thus, the edges 66 lie in a plane spaced a distance 70 (shown in FIG. 4) from the planar disposition of the edges 40 and 50 of the lingual sidewall 32 and the buccal sidewall 42, respectively.

Four notches 72, 74, 76 and 78 are formed in the lingual sidewall 32, each of the notches 72, 74, 76 and 78 intersecting the edge 36 and extending a distance through the lingual sidewall 32 to a position generally near the surface 18 of the base 12. Four notches 80, 82, 84 and 86 are formed in the buccal sidewall 42, each of the notches 80, 82, 84 and 86 intersecting the edge 46 and extending a distance through the buccal sidewall 42 to a position generally near the surface 18 of the base 12.

The notches 72 and 80 are generally aligned and each of the notches 72 and 80 are spaced an arcuate distance 88 from the end 14 of the base 12. A groove 90 is formed in the surface 18 of the base 12, the groove 90 extending generally between the sides 28 and 30 of the base 12. The groove 90 is generally aligned with the notches 72 and 80 and extends generally between the notches 72 and 80, the groove 90 cooperating with the notches 72 and 80 to form a line of structural weakness.

The notches 74 and 82 are generally aligned and each of the notches 74 and 82 are spaced on arcuate distance 92 from the end 14 of the base 12. A groove 94 is formed in the surface 18 of the base 12, the groove 94 extending generally between the sides 28 and 30 of the base 12. The groove 94 is generally aligned with the notches 74 and 82 and extends generally between the notches 72 and 82, the groove 94 cooperating with the notches 74 and 82 to form a line of structural weakness.

The notches 76 and 84 are generally aligned and each of the notches 76 and 84 are spaced an arcuate distance 96 from the end 14 of the base 12. A groove 98 is formed in the surface 18 of the base 12, the groove 98 extending generally between the sides 28 and 30 of the base 12. The groove 98 is generally aligned with the notches 76 and 84 and extends generally between the notches 76 and 84, the groove 98 cooperating with the notches 76 and 84 to form a line of structural weakness.

The notches 78 and 86 are generally aligned and each of the notches 78 and 86 are spaced an arcuate distance 100 from the end 14 of the base 12. A groove 102 is formed in the surface 18 of the base 12, the groove 102 extending generally between the sides 28 and 30 of the base 12. The groove 102 is generally aligned with the notches 78 and 86 and extends generally between the notches 78 and 86, the groove 102 cooperating with the notches 78 and 86 to form a line of structural weakness.

One end of a tab 104 is secured to the base 12, generally mid-way between the opposite ends 14 and 16 of the base 12. The tab 104 extends a distance from the base 12 in a plane generally coplanar with the surfaces 18 and 20. The tab 104 provides a means for holding the dental tray 10 during one aspect of the operation. In a preferred form, the tab 104 is removable or, in other words, can be snapped off from the base 12 so the tab 104 will not interfer with other equipment during the use of the tray 10 as, for example, when the tray 10 is mounted for use in an articulator.

In most instances, it is not desirable to utilize the full arch of the dental tray 10, the "full arch" being the dental tray 10 extending through the entire arcuate distance 22. Thus, the dental tray 10 includes the lines of structural weakness so portions of the dental tray 10 can be eliminated, thereby leaving only that portion of the dental tray 10 which is needed in a particular application. For example, the dental tray 10 can be broken along the line of structural weakness defined via the groove 90 and the notches 72 and 80 for eliminating the portion generally between the groove 90 and the end 14, thereby leaving the portion of the dental tray 10 extending between the groove 90 and the end 16 for use in a particular application.

In one other form, the dental tray 10 can be broken along the line of structural weakness defined via the groove 94 and the notches 74 and 82, thereby leaving the portion of the dental tray 10 extending between the groove 94 and the end 16 for use in a particular application. In this last-mentioned form, the eliminated portion extending between the groove 94 and the end 14 might be usable for the purpose of making models and, in fact, trays of this general shape have been available in the past. However, a tray of this last-mentioned shape extending between the groove 94 and the end 14 would not extend in a dental arch an arcuate distance sufficient to be disposable above some of the occlusal surfaces and some of the incisal edges in a manner defined via the present invention.

Also, the dental tray 10 can be broken along the line of structural weakness defined via the groove 98 and the notches 76 and 84, thereby leaving the portion of the dental tray 10 extending between the groove 98 and the end 14 for use in a particular application. Further, the dental tray 10 can be broken along the line of structural weakness defined via the groove 102 and the notches 78 and 86, thereby leaving the portion of the dental tray 10 extending between the groove 102 and the end 14 for use in a particular application. In one last form, the dental tray 10 can be broken along the line of structural weakness defined via the groove 102 and the notches 78 and 86 and it also can be broken along the line of structural weakness defined via the groove 90 and the notches 72 and 80, thereby leaving the portion of the dental tray 10 extending between the groove 90 and the groove 102 for use in a particular application.

It will be apparent to those skilled in the art that one could construct various dental trays each extending in a particular dental arch as defined via the various embodiments described above in connection with the various lines of structural weakness. However, it has been found convenient and economical simply to provide one dental tray extending the full dental arch with the lines of structural weakness, thereby allowing the dentist essentially to select the degree of the full dental arch required in a particular application utilizing the one dental tray.

In any event, regardless of whether the dental tray 10 is constructed to have a specific degree of the dental arch or is constructed to include the various lines of structural weakness, it is important that the dental tray 10 of the present invention extend through a sufficient arcuate distance such that a portion of the first surface 18 or the second surface 20 is disposable near some of the occlusal surfaces and such that a portion of the first surface 18 or the second surface 20 is disposable near some of the incisal edges or surfaces so the resulting model will extend an arcuate distance sufficient to have at least three reference points spaced for substantially preventing the model from rotating about the axis defined via the dental arch centerline 24 and for substantially preventing the model from rotating about an axis extending generally perpendicularly with respect to the dental arch centerline 24. If the arcuate distance of the dental tray 10 is less than the arcuate distance just described to provide a resulting model with at least three point references for orientation, it has been found that the resulting model can be rotated about an axis substantially parallel with the dental arch axis 24 and about an axis substantially perpendicular with respect to the dental arch axis 24, thereby leaving the proper orientation of the resulting model with respect to the model of the individual's teeth substantially a matter of judgment or educated guess. The resulting model mode made utilizing the dental tray 10 which extends a particular distance through the dental arch in the manner just described substantially eliminates the guess or speculative aspects of orientating such model with respect to the model of the individual's teeth, thereby providing a model which can be properly orientated in a faster, more economical and positive manner.

One application of the dental tray 10 is in connection with the functionally generated path technique. In general, a relatively small portion of the occlusal surface of some of the individual's teeth is removed and a relatively soft, tacky, functional wax is disposed on the prepared, occlusal surfaces. The patient then moves the upper and lower teeth into a closed, centric relation and the patient moves the teeth through multiple excursions: right lateral, right lateral protrusive, protrusive, left lateral protrusive and left lateral, for example. The excursive movements are recorded in the functional wax. A bite stone is mixed and a surface tension solution is applied directly to the surface of the functional wax having the excursive movements recorded thereon. A portion of the bite stone is applied directly to the surface of the functional wax having the excursive movements recorded thereon and the space provided via the first surface 18 and the portions of the sidewalls 32 and 42 extending the distances 34 and 44, respectively, is filled with the bite stone (sometimes referred to herein by the broader term "molding material"). The dental tray 10 filled with the bite stone then is placed in the patient's mouth in a position such that the bite stone is disposed adjacent and in contact with the surface of the functional wax having the excursive movements recorded thereon, and the dental tray 10 is held in this position until the bite stone sets or hardens. After the bite stone has set, the dental tray 10 with the hardened bite stone is removed from the patient's mouth, the surface of the bite stone having a relatively permanent impression of the excursive movements recorded in the functional wax. The dental tray 10 with the excursive movements model therein then is mounted on an articulator and utilized to shape the restorations properly in a manner accounting for such excursive movements. The functionally generated path techniques is well known in the art and some aspects and details of this technique are described in a book entitled "Evaluation, Diagnosis and Treatment of Occlusal Problems" by Peter E. Dawson, D.D.S. published by the C. V. Mosby Company, 1974, and therefore a more detailed description is not required herein.

The dental tray 10 also is useful procelain occlusal matrix techniques for constructing veneered porcelain occlusal surfaces to assure such occlusal surfaces are constructed in a manner properly considering the excursive movements. Some of the techniques and applications related to the porcelain occlusal matrix techniques are described in detail in the book entitled "Evaluation, Diagnosis and Treatment of Occlusal Problems", referred to before, and therefore a more detailed description is not required herein.

Other applications for the dental tray 10 will be apparent to those skilled in the art and the two application examples briefly described above are for example purposes only.

Changes may be made in the construction and the operation of the dental tray described herein without departing from the spirit and scope of the invention as defined in the following claims.

What is claimed is:

1. A dental tray comprising:
   a base having opposite ends, a lingual side, a buccal side, a first surface and a second surface, the base extending in a dental arch generally between the opposite ends of the base an arcuate distance at least sufficient such that a portion of the first surface is disposable generally above some portion of the occlusal surfaces and such that a portion of the first surface of the base is disposable generally above some portion of the incisal edges in one operating position of the dental tray, the dental arch extending an arcuate distance at least sufficient such that the dental tray is contactable with the occlusal surfaces and incisal edges of an individual's teeth at three reference points to substantially prevent rotation of the dental tray and resulting model about an axis generally parallel with the dental arch axis and to substantially prevent rotation of the dental tray and resulting model about an axis generally perpendicular with the dental arch axis;

a lingual sidewall connected to the lingual side of the base and extending a distance from the first surface generally perpendicularly from the base and terminating with an edge;

a buccal sidewall connected to the buccal side of the base and extending a distance from the first surface generally perpendicularly from the base and terminating with an edge, the edges of the lingual and the buccal sidewalls being disposed in a generally common plane and the lingual and the buccal sidewalls cooperating with the first surface of the base to form a space for accommodating molding material during one operating aspect of the dental tray, and the lingual sidewall and the buccal sidwall each extending a surface molding distance from the base, the surface molding distances being such that the lingual and the buccal sidewalls extend a minimum distance along the lingual and buccal edges of an individual's teeth and such that the edges of the lingual and the buccal sidewalls are each spaced a distance from the individual's gum in the one operating position of the dental tray; and a plurality of first projections connected to the first surface and spaced generally between the opposite ends of the base, each first projection being connected to the first surface and extending a distance generally perpendicularly from the first surface terminating with an edge, the edges of the first projections being disposed in a generally common plane spaced a distance generally below the planar disposition of the edges of the lingual and the buccal sidewalls, each first projection having an opening intersecting the edge and extending a distance therethrough to a position generally near the first surface.

2. A dental tray comprising:

a base having opposite ends, a lingual side, a buccal side, a first surface and a second surface, the base extending in a dental arch generally between the opposite ends of the base an arcuate distance at least sufficient such that a portion of the first surface is disposable generally above some portion of the occlusal surfaces and such that a portion of the first surface of the base is disposable generally above some portion of the incisal edges in one operating position of the dental tray, the dental arch extending an arcuate distance at least sufficient such that the dental tray is contactable with the occlusal surfaces and incisal edges of an individual's teeth at the three reference points to substantially prevent rotation of the dental tray and resulting model about an axis generally parallel with the dental arch axis and to substantially prevent rotation of the dental tray and resulting model about an axis generally perpendicular with the dental arch axis;

a lingual sidewall connected to the lingual side of the base and extending a distance from the first surface generally perpendicularly from the base and terminating with an edge, the lingual sidewall having a portion extending a distance from the second surface generally perpendicularly from the base and terminating with an edge;

a buccal sidewall connected to the buccal side of the base and extending a distance from the first surface generally perpendicularly from the base and terminating with an edge, the edges of the lingual and the buccal sidewalls being disposed in a generally common plane and the lingual and the buccal sidewalls cooperating with the first surface of the base to form a space for accommodating molding material during one operating aspect of the dental tray, and the lingual sidewall and the buccal sidewall each extending a surface molding distance from the base, the surface molding distances being such that the lingual and the buccal sidewalls extend a minimum distance along the lingual and buccal edges of an individual's teeth and such that the edges of the lingual and the buccal sidewalls are each spaced a distance from the individual's gum in the one operating position of the dental tray, the buccal sidewall having a portion extending a distance from the second surface generally perpendicularly from the base and terminating with an edge, the edges of the lingual and the buccal sidewalls being disposed in a generally common plane and the lingual and the buccal sidewalls cooperating with the second surface of the base to form a space for accommodating molding material during one operating aspect of the dental tray, and the lingual and the buccal sidewalls each extending from the second surface a surface molding distance from the base; and a plurality of projections connected to the second surface and spaced generally between the opposite ends of the base, each projection being connected to the second surface and extending a distance generally perpendicularly from the second surface terminating with the edge, the edges of the projection being disposed in a generally common plane spaced a distance generally below the planar disposition of the edges of the lingual and the buccal sidewalls extended from the second surface of the base, each projection connected to the second surface having an opening intersecting the edge and extending the distance therethrough to a position generally near the second surface.

* * * * *